United States Patent
Kalkbrenner et al.

(10) Patent No.: US 9,885,860 B2
(45) Date of Patent: Feb. 6, 2018

(54) MICROSCOPE AND METHOD FOR HIGH-RESOLUTION 3D FLUORESCENCE MICROSCOPY

(71) Applicant: Carl Zeiss Microscopy GmbH, Jena (DE)

(72) Inventors: Thomas Kalkbrenner, Jena (DE); Ralf Wolleschensky, Jena (DE)

(73) Assignee: Carl Zeiss Microscopy GmbH, Jena (DE)

( * ) Notice: Subject to any disclaimer, the term of this patent is extended or adjusted under 35 U.S.C. 154(b) by 0 days.

(21) Appl. No.: 14/373,740

(22) PCT Filed: Dec. 13, 2012

(86) PCT No.: PCT/EP2012/075465
§ 371 (c)(1),
(2) Date: Jul. 22, 2014

(87) PCT Pub. No.: WO2013/110408
PCT Pub. Date: Aug. 1, 2013

(65) Prior Publication Data
US 2015/0160446 A1    Jun. 11, 2015

(30) Foreign Application Priority Data
Jan. 24, 2012  (DE) .................. 10 2012 201 003

(51) Int. Cl.
*G01N 21/64* (2006.01)
*G02B 21/16* (2006.01)
(Continued)

(52) U.S. Cl.
CPC ......... *G02B 21/16* (2013.01); *G01N 21/6458* (2013.01); *G02B 21/361* (2013.01);
(Continued)

(58) Field of Classification Search
CPC ...... G02B 3/14; G02B 21/16; G02B 26/0825; G02B 21/0076; G02B 27/58;
(Continued)

(56) References Cited

U.S. PATENT DOCUMENTS

| 6,888,148 B2 * | 5/2005 | Wolleschensky .. G02B 21/0032 250/458.1 |
| 7,659,993 B2 * | 2/2010 | Feierabend ............... G01J 9/00 356/497 |

(Continued)

FOREIGN PATENT DOCUMENTS

| DE | 10 2006 021 317 B3 | 10/2007 |
| DE | 10 2008 009 216 A1 | 8/2009 |

(Continued)

OTHER PUBLICATIONS

Pavani, et al.;"Three-dimensional, single-molecule fluorescence imaging beyond the diffraction limit by using a double-helix point spread function";PNAS 2009;106(9):2995-2999.

(Continued)

*Primary Examiner* — Kiho Kim
(74) *Attorney, Agent, or Firm* — Duane Morris LLP

(57) ABSTRACT

A method for high-resolution 3D fluorescence microscopy, wherein fluorescence emitters in a sample are repeatedly excited to emit fluorescence, and still images are produced of the sample by means of a microscope. The microscope has an imaging beam path with an optical resolution and a focal plane, wherein the fluorescence emitters are excited to emit fluorescence in such a manner that at least a subset of the fluorescence emitters is isolated in each still image so that the images of these fluorescence emitters can be separated in the still images within the optical resolution. The positions of the fluorescence emitters are localized in the generated still images, from the images of the isolated fluorescence emitters, with a location accuracy exceeding (Continued)

the optical resolution, and a high-resolution composite image is generated therefrom.

20 Claims, 2 Drawing Sheets

(51) Int. Cl.
*G02B 21/36* (2006.01)
*G02B 27/58* (2006.01)

(52) U.S. Cl.
CPC ........... *G02B 21/367* (2013.01); *G02B 27/58* (2013.01); *G01N 2201/06113* (2013.01); *G01N 2201/12* (2013.01)

(58) Field of Classification Search
CPC .. G02B 21/002; G02B 21/361; G02B 21/367; G02B 21/58; Y10T 29/42; G01N 21/6458; G01N 2201/06113; G01N 2201/12
USPC ...................................................... 250/459.1
See application file for complete search history.

(56) References Cited

U.S. PATENT DOCUMENTS

| | | | |
|---|---|---|---|
| 7,675,045 B1 | 3/2010 | Werner et al. | |
| 7,968,856 B2* | 6/2011 | Lee | B01L 7/52 250/458.1 |
| 2002/0154398 A1 | 10/2002 | Wolleschensky et al. | |
| 2003/0142292 A1* | 7/2003 | Wolleschensky | G02B 21/0076 356/73 |
| 2003/0230710 A1* | 12/2003 | Wolleschensky | G02B 26/06 250/234 |
| 2003/0231408 A1* | 12/2003 | Wolleschensky | G02B 21/0048 359/726 |
| 2004/0242405 A1* | 12/2004 | Orme | B64G 4/00 502/101 |
| 2006/0152799 A1* | 7/2006 | Ri | G02B 21/0072 359/368 |
| 2007/0036039 A1* | 2/2007 | Kawahara | B41J 2/315 369/13.01 |
| 2007/0057211 A1* | 3/2007 | Bahlman | G01N 21/6452 250/584 |
| 2007/0268592 A1 | 11/2007 | Kam et al. | |
| 2008/0231807 A1* | 9/2008 | Lacombe | A61B 3/102 351/215 |
| 2009/0046298 A1* | 2/2009 | Betzig | G01N 21/6445 356/521 |
| 2009/0059360 A1 | 3/2009 | Evans et al. | |
| 2009/0134342 A1 | 5/2009 | Hell et al. | |
| 2009/0208072 A1* | 8/2009 | Seibel | G01N 21/4795 382/128 |
| 2009/0237501 A1 | 9/2009 | Lemmer et al. | |
| 2009/0242798 A1 | 10/2009 | Bewersdorf et al. | |
| 2009/0242801 A1* | 10/2009 | Engelhardt | G01N 21/6458 250/459.1 |
| 2009/0263002 A1 | 11/2009 | Cremer et al. | |
| 2009/0296236 A1* | 12/2009 | Bowers | G02B 27/40 359/721 |
| 2010/0160613 A1 | 6/2010 | Seyfried et al. | |
| 2010/0207037 A1 | 8/2010 | Tearney et al. | |
| 2010/0278400 A1* | 11/2010 | Piestun | G01N 21/6456 382/128 |
| 2010/0283835 A1 | 11/2010 | Bewersdorf et al. | |
| 2011/0006231 A1* | 1/2011 | Betzig | G01J 9/00 250/578.1 |
| 2011/0081653 A1* | 4/2011 | Hell | G01N 21/6428 435/6.19 |
| 2012/0074294 A1* | 3/2012 | Streuber | G01J 9/00 250/201.9 |
| 2012/0133888 A1* | 5/2012 | Gray | A61B 3/1025 351/206 |
| 2012/0224034 A1 | 9/2012 | Kalkbrenner | |
| 2012/0313012 A1* | 12/2012 | Selvin | G06T 3/4069 250/459.1 |
| 2013/0155218 A1* | 6/2013 | Kalkbrenner | G02B 21/0076 348/79 |
| 2013/0168573 A1* | 7/2013 | Yamanaka | G01N 21/6456 250/459.1 |
| 2013/0300833 A1* | 11/2013 | Soeller | G01N 21/6458 348/46 |
| 2015/0160446 A1 | 6/2015 | Kalkbrenner et al. | |

FOREIGN PATENT DOCUMENTS

| | | |
|---|---|---|
| DE | 10 2008 024 568 A1 | 12/2009 |
| DE | 10 2008 049 886 A1 | 4/2010 |
| DE | 10 2008 059 328 A1 | 6/2010 |
| DE | 10 2009 043 744 A1 | 3/2011 |
| DE | 10 2009 060 490 A1 | 6/2011 |
| DE | 10 2010 044 013 A1 | 5/2012 |
| EP | 2 437 097 A2 | 4/2012 |
| JP | 6-294739 | 10/1994 |
| JP | 06-294739 A | 10/1994 |
| JP | 2001-307366 A | 11/2001 |
| JP | 2004-21259 A | 1/2004 |
| JP | 2005-292538 A | 10/2005 |
| JP | 2013-515249 A | 5/2013 |
| WO | WO 2006/127692 A2 | 11/2006 |
| WO | WO 2010/062364 A1 | 6/2010 |
| WO | WO 2012/039636 A2 | 3/2012 |

OTHER PUBLICATIONS

Shtengel, Gleb, et al.; "Interferometric fluorescent super-resolution microscopy resolves 3D cellular ultrastructure"; PNAS 2009; 106(9):3125-3130.
Toprak, Erdal, et al.; "Three-Dimensional Particle Tracking via Bifocal Imaging", NANO Letters 2007; 7(7):2043-2045.
Juette, Manuel F., et al.; "Three-dimensional sub-100 nm resolution fluorescence microscopy of thick samples"; Nature Methods 2008; 5(6):527-529.
Huang, Bo, et al.; "Three-Dimensional Super-Resolution Imaging by Stochastic Optical Reconstruction Microscopy"; Science 2008; 319:810-813 and Supporting Online Material.
Lew, et al.;"In vivo Three-Dimensional Superresolution Fluorescence Tracking using a Double-Helix Point Spread Function"; Proceedings of SPIE 2010; 7571:75710Z-1-75710Z13.
Bourgenot C., et al.; "Adaptive Optics for Wide-Field Microscopy"; Proceedings of SPIE 2011; 7904:790414-1-790414-7.
Japanese Office Action dated Dec. 20, 2016 with English translation.

* cited by examiner

Fig. 1
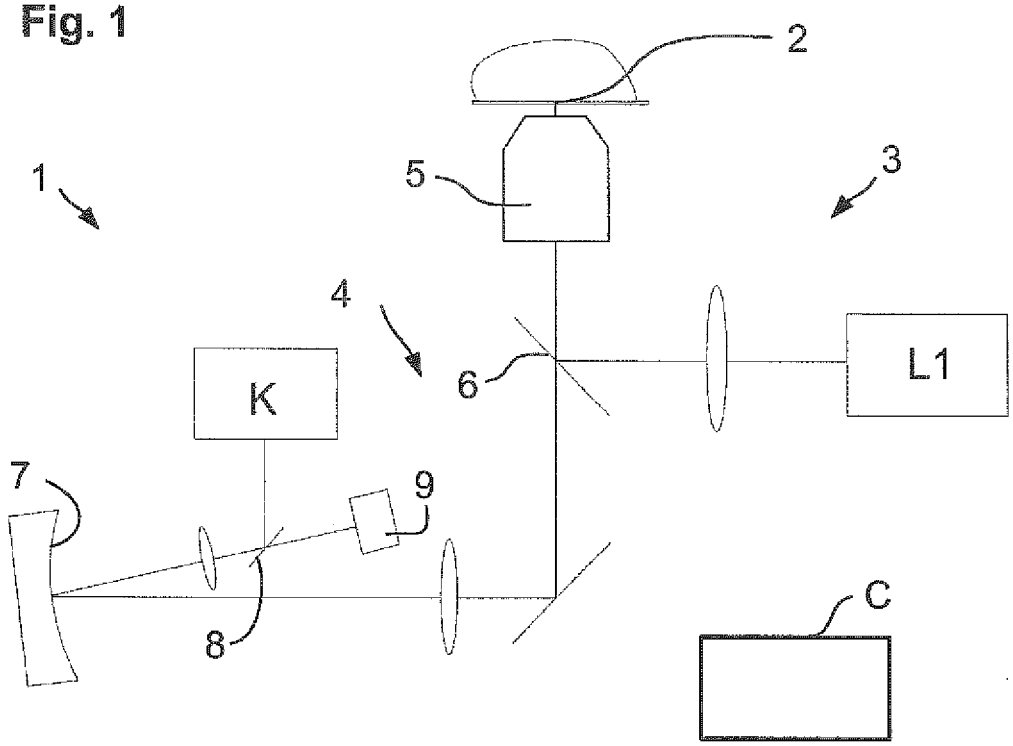
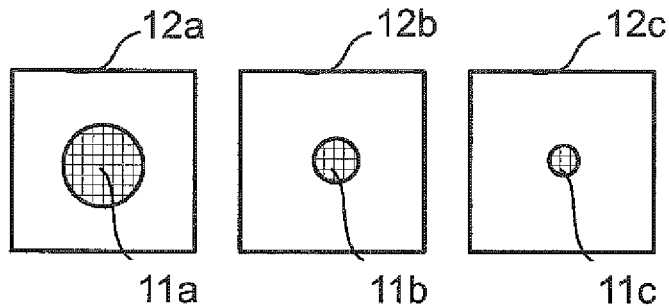
Fig. 2
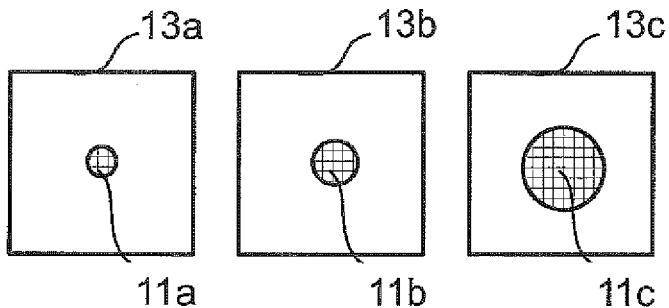
Fig. 3

MICROSCOPE AND METHOD FOR HIGH-RESOLUTION 3D FLUORESCENCE MICROSCOPY

RELATED APPLICATIONS

The present application is a U.S. National Stage application of International PCT Application No. PCT/EP2012/075465 filed on Dec. 13, 2012 which claims priority benefit of German Application No. DE 10 2012 201 003.3 filed on Jan. 24, 2012, the contents of each are incorporated by reference in their entirety.

FIELD OF THE INVENTION

The invention relates to a method for high-resolution 3D localization microscopy, wherein fluorescence emitters in a sample are repeatedly excited to emit fluorescence, and still images of the sample are produced by means of a microscope having an imaging beam path, the same having an optical resolution and a focal plane, wherein the fluorescence emitters are stimulated to emit fluorescence in such a manner that at least a subset of the fluorescence emitters is isolated in each still image, in such a manner that the images of these fluorescence emitters can be separated within the optical resolution in the still images. In the resulting still images, the positions of the fluorescence emitters are localized from the images of the isolated fluorescence emitters, with a location accuracy exceeding the optical resolution. A high-resolution composite image is generated therefrom. Each still image is divided by means of a dividing element into a first and a second sectional image, wherein the first sectional image images a first focal plane in the sample, and the second sectional image images a second focal plane in the sample, wherein both sectional images are imaged next to each other on one camera.

BACKGROUND OF THE INVENTION

The invention further relates to a fluorescence microscope for the three-dimensional imaging of a sample with a location accuracy exceeding the optical resolution, having: an illumination device which is designed for the purpose of repeatedly exciting fluorescence emitters in the sample to emit fluorescence, an imaging device having an imaging beam path with the optical resolution, designed for the purpose of producing still images of the sample at the optical resolution, a control device which is designed for the purpose of controlling the illumination device and the imaging device in such a manner that multiple still images of the sample are produced, wherein the fluorescence emitters are excited to emit fluorescence in such a manner that at least a subset of the fluorescence emitters in each still image is isolated in such a manner that the images of these fluorescence emitters can be separated in the still images within the optical resolution. The control device is also designed for the purpose of localizing the positions of the isolated fluorescing fluorescence emitters in the generated still images with a location accuracy exceeding the optical resolution, and generating a high-resolution composite image therefrom. The imaging beam path comprises a dividing element which divides each still image into a first and a second sectional image, wherein the first sectional image images a first focal plane in the sample, and the second sectional image images a second focal plane in the sample, and the imaging device includes a camera on which the two sectional images are imaged next to each other.

Various different methods have been developed in the prior art to overcome the diffraction limit in microscopy. A method, abbreviated as PALM (photo-activated light microscopy), is known from WO 2006/0127692 and DE 102006021317 A1, which uses a marking substance to image a sample, wherein said marking substance can be activated by means of optical radiation. The marking substance can only emit specific fluorescent radiation in the activated state. Inactivated molecules of the marking substance do not emit fluorescence radiation—or at least no noticeable fluorescence radiation, even after radiation with excitation light. For this reason, the excitation light is generally termed the switching signal. In the PALM method, the switching signal is applied in such a manner that at least some of the activated marking molecules are spaced apart from neighboring, activated marking molecules in such a manner that they are separated when viewed on the scale of the optical resolution of the microscope, or can be subsequently separated by image processing methods. In this case, one says that a subset of the fluorescence emitters have been isolated. After the fluorescence has been captured, the center of the radiation distribution for these isolated emitters is determined, said distribution being the result of the limit of the resolution. From this, it is possible to calculate the position of the molecules with higher precision than the optical resolution actually allows. This process is termed localization. The enhanced resolution resulting from a computational determination of the nucleus of the diffraction distribution is also termed "super resolution" in the technical literature in English. This resolution requires that at least a subset of the activated marking molecules in the sample can be differentiated—that is, isolated—at the optical resolution. Then, their position can be determined with a higher precision, and they can be localized.

To isolate individual fluorescence markers, the PALM principle exploits statistical effects. For a fluorescence marker which can be stimulated to emit fluorescence after receiving the switching signal at a given intensity, it is possible to adjust the intensity of the switching signal so that the probability of activating fluorescence markers present in a given area of the sample is so small that there is a sufficient number of sub-regions in which only fluorescence markers which can be differentiated within the optical resolution emit fluorescence.

The PALM principle has been further advanced with regards to the activation of the molecule which is targeted for detection. By way of example, for molecules which have a long-lived non-fluorescing state and a short-lived fluorescing state, a separate activation using activation light which is different in spectrum from the excitation light is not at all necessary. Rather, the sample is first illuminated with high-intensity excitation light in such a manner that the overwhelming majority of the molecules are brought into the long-lived state where fluorescence is not possible (e.g. a triplet state). The remaining molecules which are still fluorescing are thereby isolated with respect to the optical resolution.

It is also noted that the PALM principle has also been denoted in the technical literature with other abbreviations, such as STORM, for example. In this description, the abbreviation PALM is used for all microscope-based imaging which achieves a localizing resolution beyond the optical resolution of the apparatus being used, by first isolating fluorescent molecules and then localizing the same. The PALM method has the advantage that it is not necessary to have high localizing resolution for the illumination. A simple wide-field illumination is possible.

The PALM principle requires that many still images of the sample are captured, each containing subsets of isolated molecules. In order to image the sample as a whole, the number of the individual images in total must be sufficient to ensure that as many molecules as possible are at least present one time in one subset. The PALM method therefore regularly requires a plurality of still images, which requires a certain period of time for a composite image to be captured. A significantly complex calculation process is involved because a plurality of molecules must be localized in each still image. Large amounts of data are involved.

This location accuracy is only achieved laterally, by the localization in still images—that is, in a plane to which the image plane of the camera is functionally assigned. The methods are therefore limited in this respect to a two-dimensional analysis of a sample. The PALM principle is therefore combined with a TIRF excitation, which ensures that only fluorophores in a thin layer of the sample emit fluorescence.

Approaches are also known in the prior art for the localization of luminescing fluorescence markers in the third spatial dimension, which is the depth dimension with respect to the imaging of the sample. The term "depth dimension" in this case means the direction along the incident light path—that is, along the optical axis.

The publication B. Huang et al., Science 319, page 810, 2008 describes an imaging beam path for the PALM principle, wherein a weak cylindrical lens lies in the imaging beam path, thereby leading to a specific astigmatic distortion. As a result, the image of the marker on the camera is elliptically distorted as soon as the marker is positioned above or below the focal plane—that is, the symmetry point of the point spread function. The information on the depth position of the fluorescing fluorescence marker can be obtained from the orientation and the degree of the distortion. A disadvantage of this method is that the local environment and orientation of a molecular dipole can also lead to distortion of the image of the fluorescing fluorescence marker, and this distortion nevertheless has nothing to do with the depth position. Such fluorescing fluorescence markers therefore are assigned a false depth value, depending on their orientation.

The publication Pavani et al., PNAS 106, page 2995, 2009, suggests modifying the point spread function in the imaging process to give a double helix structure, by means of a spatial phase modulator. The one-dimensional images of individual, luminescing fluorescence markers then become double spots. Their depth position is encoded in the angular orientation of the common axis of the double spots.

According to the publication by Shtengel, et al, PNAS 106, page 3125, 2009, photons which are emitted by the fluorescing fluorescence markers are caused to interfere with themselves. For this purpose, two lenses which are assembled in the 4π configuration are used to simultaneously observe the fluorescing fluorescence markers. By means of a special, 3-way beam splitter, the different optical paths obtained in this manner are made to achieve interference. Each of the resulting three-point images is detected by a camera, and the proportional intensities of the three-point images provide information on the depth positions.

The publications Toprak et al., Nanolet. 7, pages 3285-3290, 2007, and Juette et al., Nature Methods 5, page 527, 2008, describe an approach wherein a 50/50 beam splitter is installed in the imaging beam path and splits the image of the sample into two sectional images which can be detected independently. In addition, an optical path length difference is inserted into one of the beam paths obtained in this manner, in such a manner that two object planes are produced from the two beam paths, which are spaced apart from each other in the z-—that is, depth—dimension by approximately half of the minimum optical resolution (for example 700 nm), or by the whole minimum optical resolution. The depth position of fluorescence markers which lie between these two planes is then obtained by analysis of the two sectional images of the same fluorescence marker (for example with respect to the width of the point spread function, which can be analyzed by a type of subtraction), or by a corresponding fitting of a three-dimensional point spread function. The method requires two highly resolved sectional images and a precise adjustment of the beam paths and calibration measurements in order to achieve a superimposition of these two sectional images with sub-pixel precision. In addition, the two sectional images of a fluorescence marker generally have a different shape because the lateral expansion of the point spread function of a system being imaged changes according to the position of the object plane being observed.

DE 102009060490 A1, which also lists further citations of literature on 3D high-resolution, likewise follows the approach according to Toprak et al. in this class, to split the image of the sample into two images.

SUMMARY OF THE INVENTION

The invention addresses the problem of improving such a method in such a manner that the construction is simplified and the requirements for alignment can be met easily.

The problem is addressed according to the invention by a method for high-resolution 3D fluorescence microscopy, wherein fluorescence emitters in a sample are repeatedly excited to emit fluorescence, and still images are produced of the sample by means of a microscope having an imaging beam path with an optical resolution and a focal plane, wherein the fluorescence emitters are stimulated to emit fluorescence in such a manner that at least a subset of the fluorescence emitters is isolated in each still image, in such a manner that the images of these fluorescence emitters can be separated within the optical resolution in the still images, in the resulting still images, the positions of the fluorescence emitters are localized from the images of the isolated fluorescence emitters, with a location accuracy exceeding the optical resolution, and a high-resolution composite image is generated therefrom. Each still image is divided by means of a dividing element into a first and a second sectional image, wherein the first sectional image images a first focal plane in the sample, and the second sectional image images a second focal plane in the sample, wherein both sectional images are imaged on at least one camera, wherein an adaptive mirror is used as the dividing element, and is substantially arranged in a pupil of the imaging beam path, wherein the adaptive mirror is adjusted in such a manner that it images the two sectional images separately in time or in space, and the adaptive mirror is adjusted in such a manner that it implements two different focal lengths for the two sectional images.

The problem is further addressed by a fluorescence microscope for the three-dimensional imaging of a sample with a location accuracy beyond the optical resolution, having: an illumination device which is designed for the purpose of repeatedly exciting fluorescence emitters in the sample to emit fluorescence, an imaging device having an imaging beam path with the optical resolution, designed for the purpose of producing still images of the sample at the optical resolution, a control device which is designed for the purpose of controlling the illumination device and the imaging device in such a manner that multiple still images of the sample are produced, wherein the fluorescence emitters are excited to emit fluorescence in such a manner that at least a subset of the fluorescence emitters in each still image is isolated in such a manner that the images of these fluorescence emitters can be separated in the still images within the optical resolution, wherein the control device is also designed for the purpose of localizing the positions of the isolated fluorescing fluorescence emitters in the generated still images with a location accuracy exceeding the optical resolution, and generating a high-resolution composite image therefrom, the imaging beam path comprises a dividing element which divides each still image into a first and a second sectional image, wherein the first sectional image images a first focal plane in the sample, and the second sectional image images a second focal plane in the sample, and the imaging device includes at least one camera on which the two sectional images are imaged next to each other, wherein the dividing element is designed as an adaptive mirror which is substantially arranged in a pupil of the imaging beam path, wherein the control device is designed for the purpose of adjusting the adaptive mirror in such a manner that it images the two sectional images separately in time or in space, and the control device is designed for the purpose of adjusting the adaptive mirror in such a manner that it implements two different focal lengths for the two sectional images.

According to the invention, an adaptive mirror is used as the beam-splitting element. It has a double function, because it both spatially separates the sectional image, and also assigns the same to different focal planes. This reduces the effort expended on alignment, which was an inherent characteristic of the principle used by the invention in the prior art.

This is implemented by, generating at least two sectional images for each still image, which are assigned to different focal planes in the sample. Then, in the sectional images, the point images of the isolated fluorophores appear with a size which depends on the depth position of the fluorophore. If the fluorophore is positioned in the focal plane of a sectional image, by way of example, the point image of the fluorescence emitter is as small as the diffraction limit allows. The point image grows with increasing distance from the focal plane, but otherwise with a constant geometry. The size of the point image of a fluorescence emitter encodes the distance from the focal plane. However, what is unknown is whether the fluorescence emitter is above or below the focal plane. For this reason, in the principle used by the invention, at least two sectional images are generated for two different focal planes in the sample in order to not only be able to determine the distance from the focal plane, but also the absolute position with respect to the focal plane. The two sectional images can be imaged on two image capture regions simultaneously or on one single image capture region consecutively.

Compared to the concepts used in the prior art, the adaptive mirror also has the advantage of greater light efficiency. The losses which arise in the prior art with beam splitters, etc., are not an issue with the solution according to the invention. Moreover, the distance between the focal planes of the two images can be adjusted over a wide range without the need to resort to a complicated mechanical actuation of optical path deflecting elements, etc. In addition, the mirror enables the imaging of the sectional images on a camera in rapid succession, because it is possible to implement a quicker change of the focal distance.

Parts of the mirror surface of the adaptive mirror, by way of example, are adjusted with a slightly different focal distance and an angle which is inclined with respect to the remaining elements, for the purpose of generating the two sectional images at the same time. The inclination leads to the desired lateral displacement and the adjacent imaging of the two sectional images on the camera.

In addition, the ratio of the intensity with which the two sectional images are generated can also be adjusted by selecting the mirror surface fraction.

Because the spatial separation of the two (simultaneously generated) sectional images—meaning the divergence of their optical axes—as well as the different focal lengths are achieved merely by a suitable controlling of the adaptive mirror, it is easy to determine and/or specify the alignment positions of the two sectional images with respect to each other. As already mentioned, the two sectional images must be aligned with respect to each other with sub-pixel precision to make it possible to achieve the desired high-resolution with depth position information.

In one particularly simple approach to the alignment of the sectional images, the same are first generated with the same focal length. At this point, two identical sectional images exist next to each other on the camera—meaning that the still image is imaged twice on the camera. It is simple at this point to obtain the reference coordinates for the two sectional images. It is only necessary for this purpose to detect a structure in the sample in the two sectional images with the required high-resolution. The coordinates of the fluorescence emitter thereby detected at high-resolution provide, in a simple manner, the relative positions of the two sectional images on the camera. Once the alignment has been carried out in this manner the mirror is controlled in such a manner that the different focal lengths are implemented. The alignment position of the sectional images does not change in this case, such that the relative specification of the coordinates in the two sectional images determined previously is still valid.

As an alternative or in addition thereto, it is also possible to make the alignment by first imaging the two sectional images on the camera superimposed, and align the positions thereof in this state. Then, the mirror is adjusted in such a manner that the two sectional images come to lie next to each other. In the process, structural elements can optionally be analyzed again.

The term "align the positions" in this case means that coordinate information is determined which makes it possible to locate a point in the second sectional image which exists in the first sectional image as well. In the simplest case, this can be a relative coordinate.

The use of the adaptive mirror makes it easy to modify the difference in the focal lengths, thereby making the depth resolution and/or the detected depth range simple to adjust.

In order to adjust the ratio of the intensities of the sectional images, the mirror surface fractions of the adaptive mirror which produce the image of the first sectional image are simply reduced in size, and the mirror surface fractions which image the second sectional image are enlarged to the same degree.

The adaptive mirror makes it particularly easy to correct imaging errors in the imaging beam path. For this purpose, it is advantageous if the radiation reflected by the mirror is (also) detected by means of a wave front sensor.

Mirrors with segmented surfaces, or continuous, so-called membrane mirrors, are particularly suitable as the adaptive mirror. These are currently known to a person skilled in the art, for example from the publication www.bostonmicromachines.com/light-modulator.htm or www.imagine-optic.com. Additionally, an overview of adaptive mirrors is found at www.wikipedia.org/wiki/Deformable_mirror.

The adaptive mirror is preferably combined with a wave front sensor which detects the wave front of the radiation which has been reflected by the mirror. In this way, imaging errors of the microscope, or imaging errors caused by the sample, are optionally corrected. Moreover, the focal plane can be displaced within certain boundaries without any problem, without the need to adjust the microscope lens. In this way, it is possible to prevent mechanical disturbances of the sample resulting from the movement of the microscope lens.

The term "image of a fluorescence emitter" should be understood to mean the generally diffraction-limited point image thereof.

It should be understood that the features named above and explained below can be used not only in the combinations given, but also in other combinations or alone, without departing from the scope of the present invention. Where method features are mentioned in this description, they are implemented in the operation of the microscope by an accordingly designed control device. Similarly, a disclosure of functional features of the control device also applies as a description of corresponding features—e.g. steps—of the method.

BRIEF DESCRIPTION OF THE DRAWINGS

The invention is described in greater detail below with reference to the attached drawings, which also disclose features which are essential to the invention, wherein:

FIG. 1 shows a schematic illustration of a microscope for depth-resolving and high-resolution fluorescence microscopy, FIGS. 2 and 3 show sectional images which are generated during the operation of the microscope 1 for the purpose of depth resolution.

DESCRIPTION OF THE EMBODIMENTS

Figure 4:
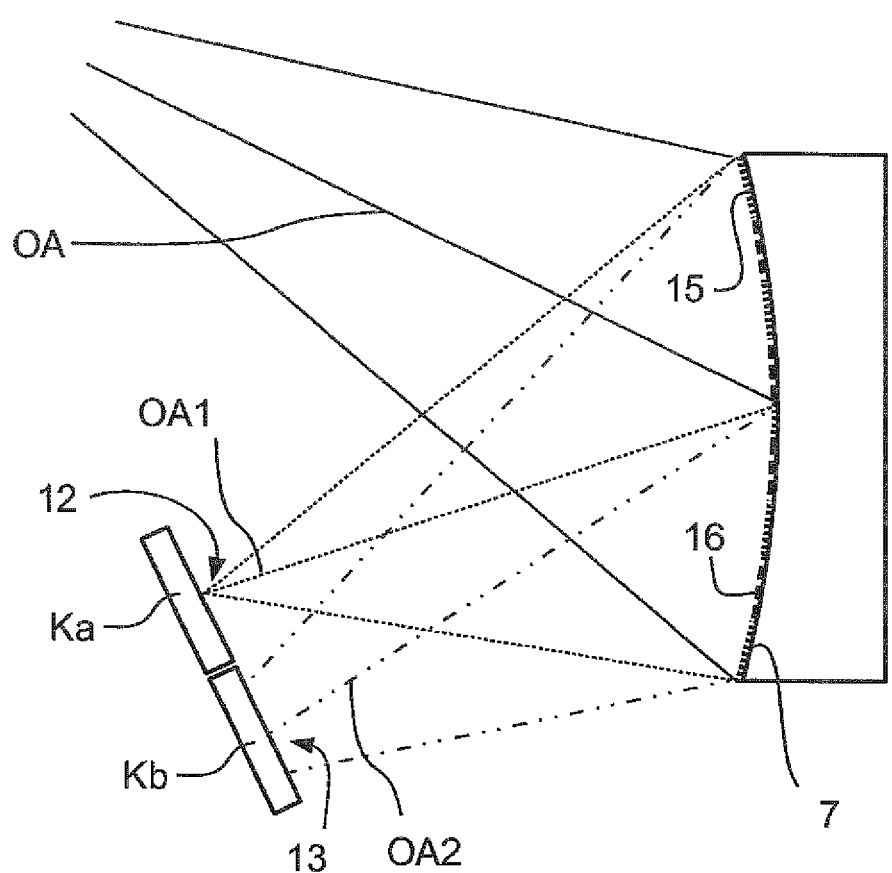
FIG. 4 shows a schematic illustration of the functionality of an adaptive mirror in the imaging beam path of the microscope in FIG. 1.

FIG. 1 schematically shows a fluorescence microscope 1, the operation of which is controlled by a control device C. It is connected to the elements and/or components of the microscope 1 via connections which are not shown. The microscope 1 is configured for the purpose of performing fluorescence microscopy according to the PALM principle, etc. It comprises an imaging beam path 3, and an imaging beam path 4. These illuminate a sample 2 and image the fluorescing sample via a common lens 5. The imaging beam path 3 is combined with the imaging beam path 4 via a beam splitter 6 which typically has a dichroic design, such that the illumination light from the imaging beam path 3 falls on the sample through the lens 5, and the imaging of the sample also occurs through the lens 5. The illumination beam path 3 can have multiple spectral channels. By way of example, only one laser source L1 is illustrated in the drawing in FIG. 1. The illumination beam path illuminates the sample in such a manner that fluorescence is excited in the sample 2. According to the design of the [implemented] PALM principle, another excitation beam source can be additionally coupled into the illumination beam path 3.

The sample 2 emits fluorescence, and the image of the fluorescing sample 2 is relayed in the imaging beam path 4 to a high-resolution camera K. The resolution of the lens 5, the imaging beam path 4, and the camera K is selected such that a diffraction-limited point image of a single fluorescence emitter falls on multiple pixels. This enables the localization, as required for the PALM principle illustrated above, of a fluorescence emitter with a lateral location accuracy which exceeds the optical resolution of the microscope 5 and the imaging beam path 4.

Of course, the microscope 1 can also be designed with multiple color channels. Then, multiple cameras are included in the imaging beam path 4, and are coupled into the beam path via suitable beam splitters.

The imaging beam path 4 includes—in additional optical elements which are not indicated in greater detail, which are not further characteristic for the microscope 1 and are otherwise conventional technical devices—an adaptive mirror 7 with a curved mirror surface which is part of the imaging beam path 4. It bundles the rays of the fluorescing sample 2 in the direction of the camera K. Its function will be explained.

The adaptive mirror is controlled by the control device C which adjusts the geometry of the mirror surface. A wave front sensor 9 which is switched via a beam splitter in the imaging beam path 4 serves the purpose of making it possible for the control device C to detect the current mirror function as precisely as possible. In this way, it increases the precision, but is not absolutely necessary.

The control device C controls the microscope 1 in such a manner that the PALM principle is executed. The sample 2 is therefore illuminated by the imaging beam path 2 in such a manner that fluorescence emitters in the sample 2 are isolated—meaning that they can be separated within the optical resolution. A plurality of still images is captured, each of which contain isolated, different subsets of the fluorescence emitters in the sample 2. In the still images, then, the position of each isolated fluorescence emitter is determined with high precision by the control device C, by means of known mathematical algorithms, such that a location accuracy which exceeds the optical resolution of the imaging is achieved. This is termed super-resolution in the literature.

The PALM principle makes possible a highly-precise lateral localization of fluorescence emitters—meaning the detection of the position perpendicular to the optical axis. The degree to which a fluorescence emitter is located in front of or behind a focal plane, within a focal plane—that is, the depth position of the fluorescence emitter—is not specified with greater precision by the PALM principle than in other wide-field microscopes.

In order to achieve better resolution in this regard—that is, to provide depth position information for the laterally localized fluorescence emitter—the microscope 1 is operated with control provided by the control device C in such a manner that each still image in which occurs the lateral localization is divided into two sectional images which are assigned to different focal planes in the sample 2. FIGS. 2 and 3 show these sectional images 12 and 13. In this case, the sectional image 12 is a still image which images a focal plane which is higher than the sectional image 13 with respect to the orientation of incident light—that is, the optical axis.

FIGS. 2 and 3 show different states a, b, c for the sectional images 12 and 13, and contain only one single fluorescence emitter by way of example. The sectional images 12a and 13a in this case show a state in which a fluorescence emitter is present in such a manner that it is in the focal plane which is assigned to the sectional image 13. As a result, the image 11a of the fluorescence emitter in sectional image 13a is a diffraction-limited spot, the size of which is the consequence of the diffraction limit. The same spot is also found in sectional image 12a, wherein the image 11a in this case is more expanded, however, because the imaged fluorescence emitter is not in the focal plane of the sectional image 12. This leads to a defocussing which enlarges the image 11a. The comparison of the images 11a in the sectional image 12a and 13a clearly shows the focal plane of the fluorescence emitter, particularly in the focal plane of the sectional image 13.

The control device C can therefore derive corresponding depth position information for the fluorescence emitters from the size of the point images of the fluorescence emitter and the comparison of the sectional images. The lateral localization is obtained, as is known, from the point image 11a.

The sectional images 12b and 13b show a state in which a fluorescence emitter is located between the focal planes of the sectional images. This can be recognized by the fact that the point image 11b of the fluorescence emitter has a size which is greater than the diffraction-limited minimum size, but is also less than the size which would result if the fluorescence emitter were positioned in the focal plane of the sectional image 13.

The sectional images 12c and 13c finally show a state which is inverted with respect to the state a.

The concept of obtaining not only a relative position of the fluorescence emitters with respect to the focal plane of an image, but also the direction of the displacement with respect to the focal plane, using sectional images from different focal planes, is known in the prior art, as described above.

The fluorescence microscope 1 arrives at the sectional images 12 and 13 by using the adaptive mirror 7. This both functions to divide the image of the sample 2 into two sectional images 12, 13, and also to assign the same to different focal lengths using different focal distances for the sectional images 12, 13. This is illustrated schematically in FIG. 4, which shows the adaptive mirror 7, wherein radiation from the sample 2 falls on the same along an optical axis OA. The reflecting surface of the mirror 7 is divided into segments 15 and 16, and/or is divided into such segments by means of the control provided by the control device 10. The adaptive mirror functions as a beam splitter which divides the diffracted still image of the sample 2 in the imaging beam path 4 into the two sectional images 12 and 13. Further imaging elements such as lenses, etc. can be used in this case, but are not included in the illustration in FIG. 4—to allow better understanding.

The adaptive mirror 7 is adjusted in such a manner that it has mirror surface segments 15 which deflect the optical axis OA in a first direction. In addition, interlaced mirror surface segments 16 deflect the optical axis OA in a second direction. The first direction in this case is an optical axis OA1 which is functionally assigned to the camera image region Ka, and the second direction corresponds to an optical axis OA2 which is functionally assigned to the camera image region Kb. The corresponding peripheral rays for the imaging by the first mirror surface segment 15 in this case are sketched with a dotted line in FIG. 4, as is the optical axis OA1, while the peripheral rays and the optical axis OA2 directed through the mirror surface segment 16 to the camera image region Kb are drawn with a dashed line.

The mirror surface segments 15 also produce a focal distance difference in the generated sectional image 12. The adaptive mirror 7 is therefore adjusted in such a manner that it not only generates an image division, but also assigns the two sectional images 12 and 13 to different focal planes in the sample 2. This can be recognized by the fact that the peripheral rays for the sectional image 12 meet at the optical axis OA in the camera image region Ka, whereas the dashed peripheral rays for the sectional image 13 are spread out further in the camera image region Kb.

The camera image regions Ka and Kb are preferably, but not absolutely necessarily, image regions of one and the same camera K. This has the advantage that an alignment of the sectional images 12 and 13 can be easily performed with sub-pixel precision. The following options for this can be contemplated, among others:

1. In an alignment step performed prior to the actual measurement process, the adaptive mirror 7 is adjusted in such a manner that the sectional images 12 and 13 are generated along diverging optical axes OA1 and OA2—but with the same focal distance of the mirror 7. The sectional images 12 and 13 then are created during the alignment step from the same focal plane. The high-resolution lateral localization of one or more structures in the sectional images 12 and 13 then makes it easy to obtain a reference specification, by means of which structures in the sectional image 12 can be converted to the coordinate system of the sectional image 13, and vice-versa, during the later measurement operation.

2. If the camera image regions Ka and Kb are image regions of one and the same camera, the sectional images 12 and 13 are first superimposed—meaning depicted overlapping each other. The mirror 7 is then adjusted in such a manner that the optical axes OA1 and OA2 align, wherein the angular difference between the mirror segments 15 and 16 is therefore no longer present. In this overlapping position, it is easy to ensure that the images lie one over the other, despite the different focal distances of the segments 15 and 16. In addition, a referencing of the images to each other can be carried out in a simple manner. Then, in the alignment step, the mirror is moved in such a manner that the angular difference between the mirror segments 15 and the mirror segments 16 is present. In other words, the angle divergence between the optical axes OA1 and OA2 appears, and the sectional images 12 and 13 lie next to each other. The difference in the coordinates between the sectional images 12 and 13 produced as a result can be easily derived from the mirror parameters, such that a highly-precise relative referencing between the sectional images 12 and 13 is ensured by the previously implemented alignment in the superimposed state.

Of course, the method steps 1 and 2 indicated above, which are carried out prior to the actual measuring principle for the purpose of alignment, can also be used in any arbitrary sequence and/or can be combined.

While the invention has been illustrated and described in connection with currently preferred embodiments shown and described in detail, it is not intended to be limited to the details shown since various modifications and structural changes may be made without departing in any way from the spirit of the present invention. The embodiments were chosen and described in order to best explain the principles of the invention and practical application to thereby enable a person skilled in the art to best utilize the invention and various embodiments with various modifications as are suited to the particular use contemplated.

What is claimed is:

1. A method for high-resolution 3D fluorescence microscopy in wide-field imaging, comprising
(a) exciting fluorescence emitters in a sample in a microscope having a wide-field imaging beam path with an optical resolution to emit fluorescence, said fluorescence emitters being stimulated to emit fluorescence in such a manner that at least in a subset of the fluorescence emitters said stimulated fluorescence emitters are isolated from each other so that the images of these fluorescence emitters can be optically separated by said microscope within the optical resolution of said microscope, (b) wide-field imaging a first focal plane into a first partial image and a second focal plane different from the first focal plane into a second partial image, wherein a deformable mirror, located in a pupil of the imaging beam path, is adjusted to select the first focal plane and the second focal plane, and recording the first and second images in first and second partial image frames, (c) calculating from the partial image frames, the positions of said fluorescence emitters with a location accuracy exceeding the optical resolution, and (d) generating a high-resolution composite image from the detected positions.

2. The method according to claim 1, wherein said deformable mirror images the two partial images along diverging optical axes, in adjacent image capture regions.

3. The method according to claim 2, further comprising adjusting an intensity ratio of the partial images by mirror surface fractions of the deformable mirror, which provide the imaging of the first partial image, being reduced in size, wherein mirror surface fractions of the deformable mirror which provide the imaging of the second partial image are enlarged by the same degree.

4. The method according to claim 2, wherein said two partial images are generated on different areas of the same camera or on different cameras.

5. The method according to claim 1, further comprising changing a difference in the focal lengths by means of the adjustment of the deformable mirror to implement the adjustment of a depth resolution or a detected depth region.

6. The method according to claim 5, wherein said deformable mirror images the two partial images consecutively along the same optical axis in an image capture region of a same camera.

7. The method according to claim 1, further comprising detecting radiation reflected by the mirror by means of a wave front sensor, and the mirror is adjusted for the purpose of correcting imaging errors of the imaging beam path or imaging errors caused by the sample.

8. The method according to claim 1, further comprising adjusting the two focal lengths synchronously for a depth position adjustment.

9. The method according to claim 1, wherein prior to the depth-resolving microscopy process, the partial images are first generated with the same focal length, and positionally aligned in this state, in an alignment step of the partial images.

10. The method according to claim 1, wherein two image capture regions are on one camera, and prior to the depth-resolving microscopy process, in an alignment step, the two partial images are first imaged superimposed on the camera and positionally aligned in this state, and then the mirror is adjusted in such a manner that the partial images come to lie next to each other in the image capture regions.

11. The method according to claim 1, wherein steps (a)-(c) are repeated before step (d).

12. The method according to claim 1, wherein said stimulation in step (a) comprises activating said fluorescence emitters from a state in which they are unable to emit fluorescence to a state in which they are able to emit fluorescence.

13. A fluorescence microscope for the purpose of three-dimensional wide-field imaging of a sample with a location accuracy exceeding the optical resolution, comprising:

an illumination device designed for the purpose of repeatedly exciting fluorescence emitters in the sample to emit fluorescence, a wide-field imaging device having an imaging beam path with an optical resolution designed for the purpose of recording a series of image frames of the sample at the optical resolution, a control device which is designed for the purpose of controlling the illumination device and the imaging device in such a manner that a series of image frames of the sample are produced, wherein the fluorescence emitters are excited to emit fluorescence in such a manner that at least a subset of the fluorescence emitters is isolated in each individual frame in such a manner that the images of these fluorescence emitters can be separated in the image frames within the optical resolution, each image frame comprising a first and a second partial image frame by means of a deformable mirror arranged in a pupil of the imaging beam path, said first partial image frame being a wide field image of a first focal plane in the sample, and said second partial image frame being a wide field image of a second focal plane in the sample, said first and second focal planes being different, and both said first and second sectional image frames being recorded separately, the control device being designed for the purpose of detecting the positions of the isolated fluorescing fluorescence emitters in the generated sectional image frames with a location accuracy exceeding the optical resolution, and of generating a high-resolution composite image therefrom, the imaging device having at least one camera on which the two partial image frames are imaged, the control device being designed for the purpose of adjusting the deformable mirror in such a manner that it images the two image frames separately in time or in space, and the control device being designed for the purpose of adjusting the deformable mirror in such a manner that it implements two different focal lengths for the two partial image frames.

14. The fluorescence microscope according to claim 13, wherein the control device is designed for the purpose of controlling the deformable mirror in such a manner that it images the two partial images along diverging optical axes, in adjacent image capture regions of the camera.

15. The fluorescence microscope according to claim 14, wherein said control device is designed for the purpose of adjusting the deformable mirror, for the purpose of adjusting an intensity ratio of the partial images, in such a manner that the size of mirror surface fractions of the deformable mirror which provide the imaging of the first partial image is reduced, and the size of mirror surface fractions of the deformable mirror which provide the imaging of the second partial image is enlarged by the same degree.

16. The fluorescence microscope according to claim 13, wherein the control device is designed for the purpose of adjusting the deformable mirror in such a manner that a difference in the focal lengths is changed, for the purpose of implementing the adjustment of a depth resolution or a detected depth region.

17. The fluorescence microscope according to claim 13, further comprising a wave front sensor which detects radiation reflected by the mirror in order to adjust the mirror for the purpose of correcting imaging errors of the imaging beam path.

18. The fluorescence microscope according to claim 13, wherein said control device is designed for the purpose of adjusting the two focal lengths synchronously, for a depth position adjustment.

19. The fluorescence microscope according to claim 13, wherein said control device is designed for the purpose of controlling the mirror in such a manner that the partial images are first generated with the same focal length, and a position alignment signal is generated in this state, for the purpose of alignment prior to the depth-resolving imaging process.

20. The fluorescence microscope according to claim 13, wherein said image capture regions are provided by a camera, and the control device is designed for the purpose of controlling the mirror in such a manner that the partial images are depicted superimposed on the camera, a position alignment signal is generated in this state, and then the mirror is adjusted in such a manner that the partial images are imaged next to each other in the image capture regions, for the purpose of alignment prior to the depth-resolving measurement process.

* * * * *